(12) United States Patent
Furey et al.

(10) Patent No.: US 10,557,811 B2
(45) Date of Patent: Feb. 11, 2020

(54) SENSOR FITTING FOR BIOTECH PROCESS BAG

(71) Applicant: PendoTECH, Princeton, NJ (US)

(72) Inventors: James F. Furey, Plainsboro, NJ (US); Dennis C. Annarelli, Newton, PA (US); John Benson, Yardley, PA (US)

(73) Assignee: Pendotech, Princeton, NJ (US)

( * ) Notice: Subject to any disclaimer, the term of this patent is extended or adjusted under 35 U.S.C. 154(b) by 0 days.

(21) Appl. No.: 15/909,556

(22) Filed: Mar. 1, 2018

(65) Prior Publication Data
US 2018/0224386 A1 Aug. 9, 2018

Related U.S. Application Data

(63) Continuation-in-part of application No. 15/101,661, filed as application No. PCT/US2014/068866 on Dec. 5, 2014, now Pat. No. 10,041,896.

(60) Provisional application No. 61/912,884, filed on Dec. 6, 2013.

(51) Int. Cl.
*A61M 5/14* (2006.01)
*G01N 27/07* (2006.01)

(52) U.S. Cl.
CPC .................. *G01N 27/07* (2013.01)

(58) Field of Classification Search
CPC ............ B01F 15/0085; B01F 15/00831; B01F 13/0827; B01F 15/00207; B01F 7/162; C12M 23/14; C12M 27/02; C12M 29/06; G01D 11/30
See application file for complete search history.

(56) References Cited

U.S. PATENT DOCUMENTS

| | | | |
|---|---|---|---|
| 4,315,990 A | 2/1982 | Sheets | |
| 4,375,864 A * | 3/1983 | Savage | B65D 77/067 222/81 |
| RE32,354 E | 2/1987 | Savage | |
| 5,609,195 A * | 3/1997 | Stricklin | F16L 37/28 137/614.04 |
| 6,523,426 B1 | 2/2003 | Vincent et al. | |
| 6,852,216 B2 | 2/2005 | Moscaritolo et al. | |
| 7,226,207 B2 | 6/2007 | Feldmeier | |
| 7,329,338 B2 | 2/2008 | Sieth et al. | |
| 7,469,884 B2 | 12/2008 | Terentiev et al. | |
| 7,603,921 B2 | 10/2009 | Baumfalk et al. | |
| 7,832,296 B2 | 11/2010 | Klees et al. | |
| 7,924,169 B2 | 4/2011 | Baumfalk et al. | |

(Continued)

FOREIGN PATENT DOCUMENTS

DE 100 03 436 A1 9/2000
DE 10 2004 015 703 A1 11/2005
(Continued)

*Primary Examiner* — Alesa Allgood
(74) *Attorney, Agent, or Firm* — Hoffmann & Baron, LLP

(57) ABSTRACT

A fluid process application bag includes a flexible film body having an opening, a port plate sealed around the opening of the flexible film body, a sensor fitting and a sensor contained within the sensor fitting. The port plate has a receptacle defining a passage in fluid communication with an interior of the flexible film body and the sensor fitting has a body portion seated within the passage of the receptacle and is coupled to the receptacle. The sensor has at least one probe communicating with the interior of the flexible film body.

12 Claims, 11 Drawing Sheets

(56) References Cited

U.S. PATENT DOCUMENTS

| | | |
|---|---|---|
| 8,123,397 B2 | 2/2012 | Baumfalk et al. |
| 8,292,491 B2 | 10/2012 | Castillo et al. |
| 8,302,496 B2 | 11/2012 | Furey et al. |
| 8,544,352 B2 | 10/2013 | Glatzel et al. |
| 8,550,439 B2 | 10/2013 | Terentiev et al. |
| 10,001,454 B2 | 6/2018 | Schick et al. |
| 2005/0163667 A1 | 7/2005 | Krause |
| 2008/0053255 A1 | 3/2008 | Furey et al. |
| 2008/0206847 A1* | 8/2008 | Kunas .................. B01F 7/001 435/287.1 |
| 2009/0290005 A1 | 11/2009 | Wanibe et al. |
| 2010/0129899 A1 | 5/2010 | Oosterhuis et al. |
| 2010/0301060 A1 | 12/2010 | Bernard et al. |
| 2011/0013474 A1 | 1/2011 | Ludwig et al. |
| 2011/0249526 A1 | 10/2011 | Wong |
| 2011/0260738 A1 | 10/2011 | Selman et al. |
| 2012/0144894 A1 | 6/2012 | Trapp et al. |
| 2012/0244608 A1 | 9/2012 | Selker et al. |
| 2012/0301954 A1 | 11/2012 | Ehring et al. |
| 2013/0029374 A1 | 1/2013 | Eberheim et al. |
| 2013/0036843 A1 | 2/2013 | Pfauch et al. |
| 2013/0036844 A1* | 2/2013 | Furey .................. G01D 11/30 73/866.5 |
| 2013/0121104 A1 | 5/2013 | Castillo et al. |
| 2013/0145818 A1 | 6/2013 | Allgauer et al. |
| 2013/0288359 A1 | 10/2013 | Loebbert et al. |
| 2014/0124504 A1 | 5/2014 | Bernard et al. |

FOREIGN PATENT DOCUMENTS

| | | |
|---|---|---|
| DE | 20 2007 000152 U1 | 4/2007 |
| EP | 2973103 A2 | 1/2016 |
| WO | 01/27564 A1 | 4/2001 |
| WO | 2005/068059 A1 | 7/2005 |
| WO | 2011/071897 A2 | 6/2011 |
| WO | 2012/152423 A1 | 11/2012 |
| WO | 2013/011231 A1 | 1/2013 |
| WO | 2013/063550 A1 | 5/2013 |
| WO | 2013/158312 A1 | 10/2013 |

\* cited by examiner

SENSOR FITTING FOR BIOTECH PROCESS BAG

CROSS-REFERENCE TO RELATED APPLICATION

This is a continuation-in-part of U.S. Ser. No. 15/101,661, filed Jun. 3, 2016, which claims the benefit of U.S. Provisional Application No. 61/912,884, filed Dec. 6, 2013, which is incorporated herein by reference in its entirety for all purposes.

BACKGROUND

Process applications generally involve a series of actions or steps that are taken in a prescribed sequence in the development and/or manufacturing of a product. Such processes are repeatable and predictable, or at least are generally intended to be. In a wide range of fluid handling process applications knowledge of process conductivity or other fluid characteristics is a valuable piece of information. Such measurements are of particular interest in the technology field of biopharmaceutical process applications for both product development and manufacturing.

For example, in order to measure conductivity in a fluid stream, an in-line gauge is traditionally provided somewhere along the fluid flow path. However, the use of an in-line gauge is not optimal in some process applications. For example, when using lightweight flexible tubing, such in-line devices can be bulky, weighty or too intrusive. Alternatively, to measure conductivity and/or temperature in a vessel, a gauge is inserted into a vessel port. However, in a lightweight, collapsible thin-walled vessel, such a bag insertion of a traditional gauge is not optimal Additionally, many fluid process applications in biotechnology require a fluid handling environment with minimal microbial contamination. It is important to ensure that an uncontaminated environment has been maintained throughout the process. Thus, in critical processes, such as production in bioreactors, filtration, chromatography, and formulation and filling of containers or vials, knowledge of the conductivity or other fluid characteristics in the process is critical, but an uncontaminated environment must be maintained.

One method of maintaining an uncontaminated environment is to employ critical assembly elements that are designed for single-use (or limited use). Thus, such an assembly could contain a large variety of components such as flexible tubing, single use process containers, such as plastic/polymeric bags. Such bags are commonly used in biotech processes for storage of fluids and mixing.

These process bags are typically made of polymeric film materials such as polyethylene (PE) film material and are often provided with port plates, which are attached to the film material before the material is made into a bag. The plates are also made of a similar molded polymeric material and are melt-sealed to the film for the required penetrations for tubing, sample ports, etc.

As mentioned above, there is often a need to measure a physical characteristic or parameter, such as conductivity and/or temperature, of the fluid within a process system, and such measurements are typically taken by sensors provided somewhere within the tubing defining the fluid flow path.

However, in certain instances, it would be desirable to measure such characteristic or parameter of the fluid within the process bag, particularly for mixing of fluids with salts for critical processes or making an addition to adjust a parameter of the fluid. However, the polymers used for fabricating innovative plastic in-line conductivity sensors may be of a material that cannot be heat sealed to the film material. Moreover, adhesives or glues of any type would not be desired in such contamination-free environments and would likely not even work. Also, if sterilization is required, many single-use process bags are not compatible with most heat sterilization temperatures so gamma or ethylene oxide (ETO) processing is typically used so the process sensors should be compatible with gamma or ETO processing.

It is therefore desirable to provide a sensor that is suitable for simple and easy removable connection with a biotech process bag, while providing the ability to accurately measure properties, such as conductivity and/or temperature, of the fluid within the bag. Also, the sensor and bag fitting must be easy to use, inexpensive and universally adaptable to numerous applications.

SUMMARY

According to an aspect of the invention, a sensor connection for a fluid process application bag is provided. The fluid process application bag is generally a flexible film body having an opening. A port plate is sealed around the opening of the fluid process application bag and has a receptacle defining a passage in fluid communication with an interior of the fluid process application bag. A sensor fitting having a body portion is seated within the passage of the receptacle and is coupled to the receptacle. A sensor is contained within the sensor fitting and the sensor has at least one probe communicating with the interior of the fluid process application bag.

In a preferred embodiment, the sensor is a conductivity sensor having two or more probes communicating with the interior of the fluid process application bag, wherein a temperature sensor is placed within one of the probes and the conductivity is measured by at least two of the probes.

In one embodiment, the body portion of the sensor fitting includes a threaded portion for threadable engagement with a threaded portion provided in the receptacle of the port plate.

In an alternative embodiment, the body portion of the sensor fitting includes at least one tab extending radially outwardly from the body portion and the receptacle of the port plate includes a discontinuous rib extending radially inwardly into the passage. The tab engages the rib for releasably securing the sensor fitting in the port plate.

In another alternative embodiment, the body portion of the sensor fitting and the receptacle of the port plate include cooperating detent structure for providing snap-fit engagement between the sensor fitting and the port plate. The detent structure may include a sloped flank extending radially outwardly from the body portion of the sensor fitting and an oppositely sloped flank extending radially inwardly into the passage of the receptacle of the port plate.

The sensor fitting preferably includes an O-ring fitted around the body portion, wherein the O-ring provides a seal between the body portion of the sensor fitting and the receptacle of the port plate. Alternatively, the O-ring can be provided in the receptacle at a suitable location so as to provide a seal between the sensor fitting and the receptacle.

In a preferred embodiment, the body portion of the sensor fitting is cup-shaped and has a side wall and a bottom defining an internal compartment for receiving the sensor, wherein at least one of the probes of the sensor extends through the bottom. In this case, the sensor fitting further preferably includes a head portion covering the internal compartment and an electrical lead of the sensor extends through the head portion.

The port plate further preferably includes a skirt portion extending outwardly from the receptacle, wherein the skirt portion is heat sealed to the fluid process application bag.

Features of the disclosure will become apparent from the following detailed description considered in conjunction with the accompanying drawings. It is to be understood, however, that the drawings are designed as an illustration only and not as a definition of the limits of this disclosure.

BRIEF DESCRIPTION OF THE DRAWINGS

FIG. 5a is a plan view of the port plate shown in FIG. 5 taken along line 5a-5a.

FIG. 7a is a cross-sectional view of the port plate shown in FIG. 7 taken along the line 7a-7a.

DETAILED DESCRIPTION

Figure 1:
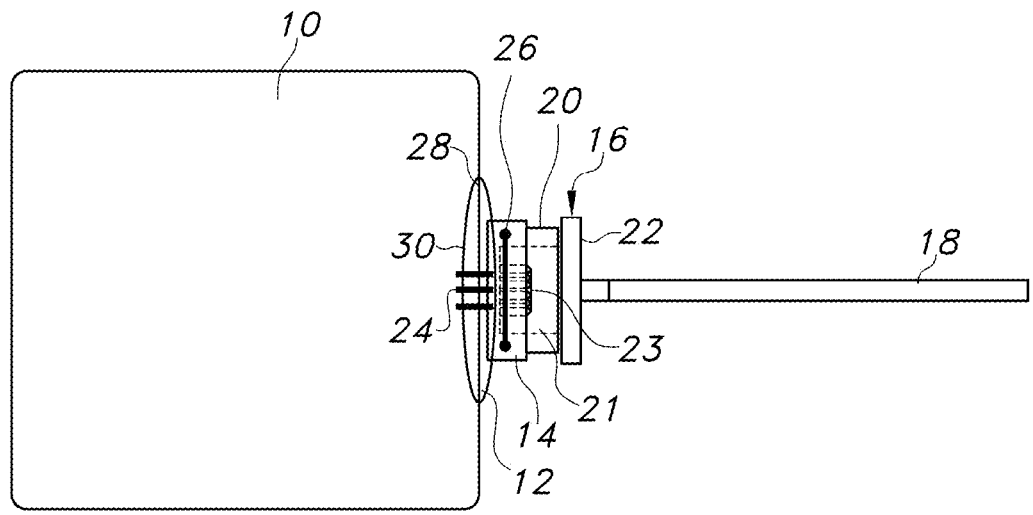
FIG. 1 is an illustration of a sensor fitting attached to a biotech process bag in accordance with the subject invention.
Figure 2:
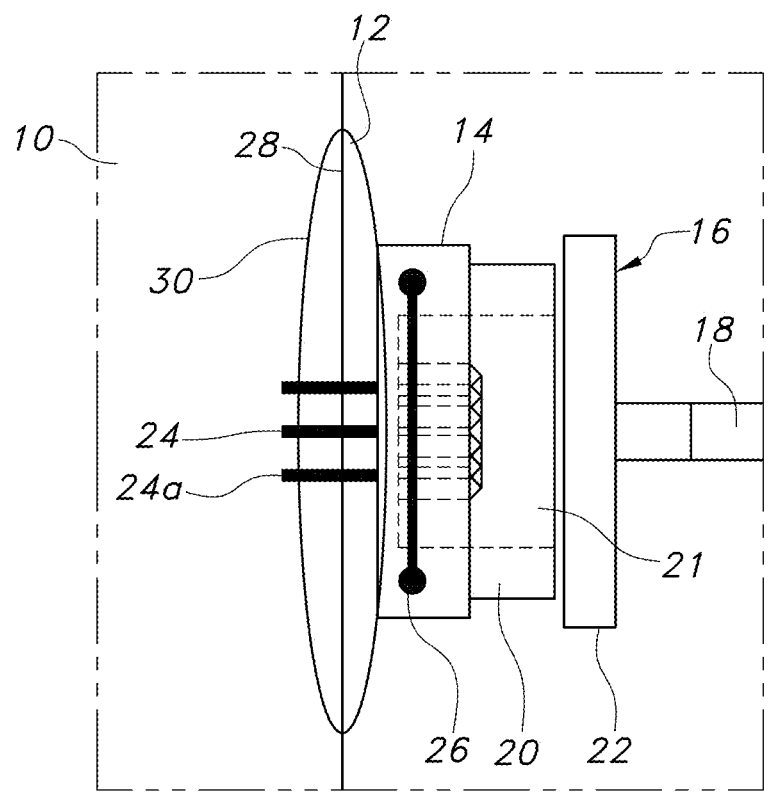
FIG. 2 is an enlarged view of the sensor fitting attached to the biotech process bag shown in FIG. 1.

Looking first at FIGS. 1 and 2, a flexible storage bag 10 is provided with a specially designed port plate 12 having a receptacle 14 to accept a sensor fitting 16 according to the present invention. The sensor fitting 16 may contain any type of sensor desired for measuring a physical property of the fluid within the process bag. Such sensors may include, but are not limited to conductivity sensors, temperature sensors, pressure sensors, pH sensors, and sensors for various types of absorbance measurements, such as UV, visible or near infrared light waves.

The sensor is typically hard wired for suitable connection to external measuring equipment (not shown) via a cable 18. However, other means for communication with the sensor, such as wireless communication or fiber optic connection for light-based measurements, may be employed.

The sensor fitting 16 is somewhat similar to the conductivity sensor connector shown and described in commonly owned U.S. Pat. No. 8,302,496, the specification of which is incorporated herein by reference. However, the sensor fitting 16 of the present invention is specially made without the hose barb/fluid flow portion of the connector disclosed in the '496 patent. Thus, the sensor fitting 16 of the present invention generally includes a body portion 20 and a head portion 22 provided at one end of the body portion, which together form a housing defining an inner compartment for containing the desired sensor therein.

The body portion 20 is cup-shaped with a side wall and a bottom defining a compartment 21 therein for receiving the sensor 23. The head portion 22 may be molded separately from the body portion 20 and may be fixed to the open end of the side wall, opposite the bottom, to seal the compartment 21. The bottom may be provided with suitably sized apertures, through which one or more leads 24 of the sensor can extend and protrude outwardly from the body portion from the compartment.

Thus, the body portion 20 is designed to permit one or more probes or electrodes 24 of the sensor to extend outwardly from one end of the fitting in a fluid-tight manner, while the head portion 22 is designed to permit electrical connection between the external cable 18 and the sensor. In a preferred embodiment shown in the drawings, a conductivity/temperature sensor 23 is shown contained in the sensor fitting 16, which has three (3) conductivity probes 24 protruding from the bottom of the body portion 20 opposite the head portion 22. One probe 24a contains a thermistor, or other temperature measuring element, such as a thermocouple or RTD, of the sensor 23 to measure temperature, while all probes are electrically connected to the conductivity measuring component of the sensor. However, as mentioned above, any type of sensor can be contained within the fitting, The body portion 20 of the sensor fitting 16 is preferably generally cylindrically shaped and is sized to fit snugly within the correspondingly sized receptacle 14 of the port plate 12. Thus, the sensor fitting 16 is preferably molded with tight tolerances from a high-performance polymer, such as polysulfone, so that the sensor fitting can be inserted and sealed into the receptacle 14 of the port plate 12 to prevent any fluid from leaking around the interface of the sensor.

Figure 4:
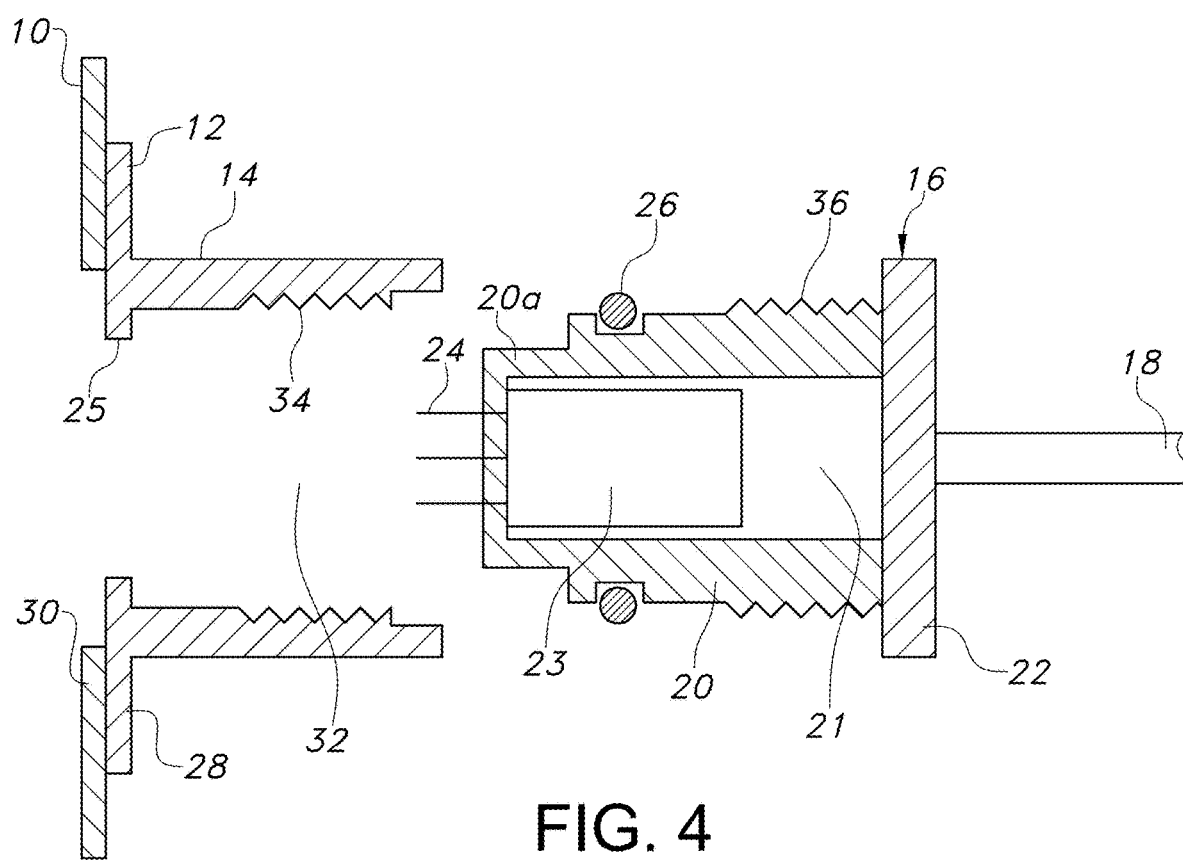
FIG. 4 is a cross-sectional view of a first embodiment of the connection between the sensor fitting and the port plate.

When fully seated in the bottom of the receptacle 14 in the port plate 12, the bottom of the compartment cylinder of the sensor fitting body portion 20 should be as close as possible to be flush with the wall of the bioprocess bag 10 so the electrodes 24 would protrude as much as possible into the bag and not sit in a dead leg. Thus, as shown in FIG. 4, the body portion 20 may be provided with a reduced diameter extension 20a at its bottom that is sized to fit through a hole 25 formed in the port plate. In this manner, the bottom of the sensor fitting will be flush with the wall of the bag and the electrodes 24 will protrude as far as permissible into the bag.

An O-ring 26 is also preferably provided between an inner surface of the receptacle 14 and an outer surface of the sensor fitting body portion 20 so as to provide a fluid tight seal therebetween. The O-ring 26 may be seated in a groove formed in the body portion 20 of the sensor fitting 16 to prevent axial movement of the ring.

Figure 3:
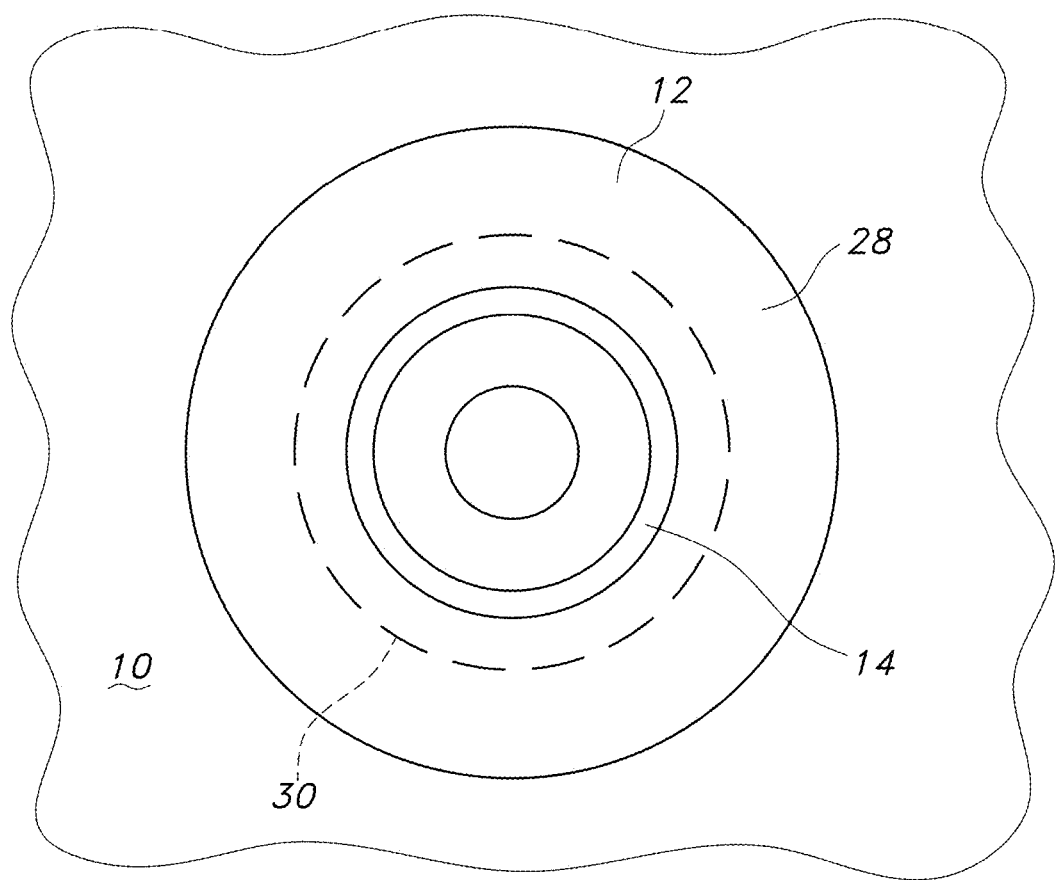
FIG. 3 is a plan view of the port plate shown in FIGS. 1 and 2.

Referring additionally to FIG. 3, the receptacle 14 of the port plate 12 preferably has a circular cross-section and a thin skirt portion 28 of the port plate extends outwardly from the receptacle 14. The skirt portion 28 is heat sealed around a hole 30 formed in the process bag 10 in a conventional manner. The receptacle 14 and skirt portion 28 define an opening 25 communicating with the interior of the process bag 10 via the hole 30 formed in the process bag. The receptacle 14 further forms a passage way 32 communicating with the opening 25 to receive the sensor fitting 12.

The sensor fitting 16 is seated within the passage way 32 and can be attached to the receptacle 14 in several ways. For example, FIGS. 4 and 4a show an embodiment where the inner surface of the receptacle 14 is provided with internal threads 34 and the outer surface of the sensor fitting body portion 20 is provided with external threads 36, which cooperatively engage the internal threads of the receptacle to attach the sensor fitting 16 to the receptacle.

Figure 4A:
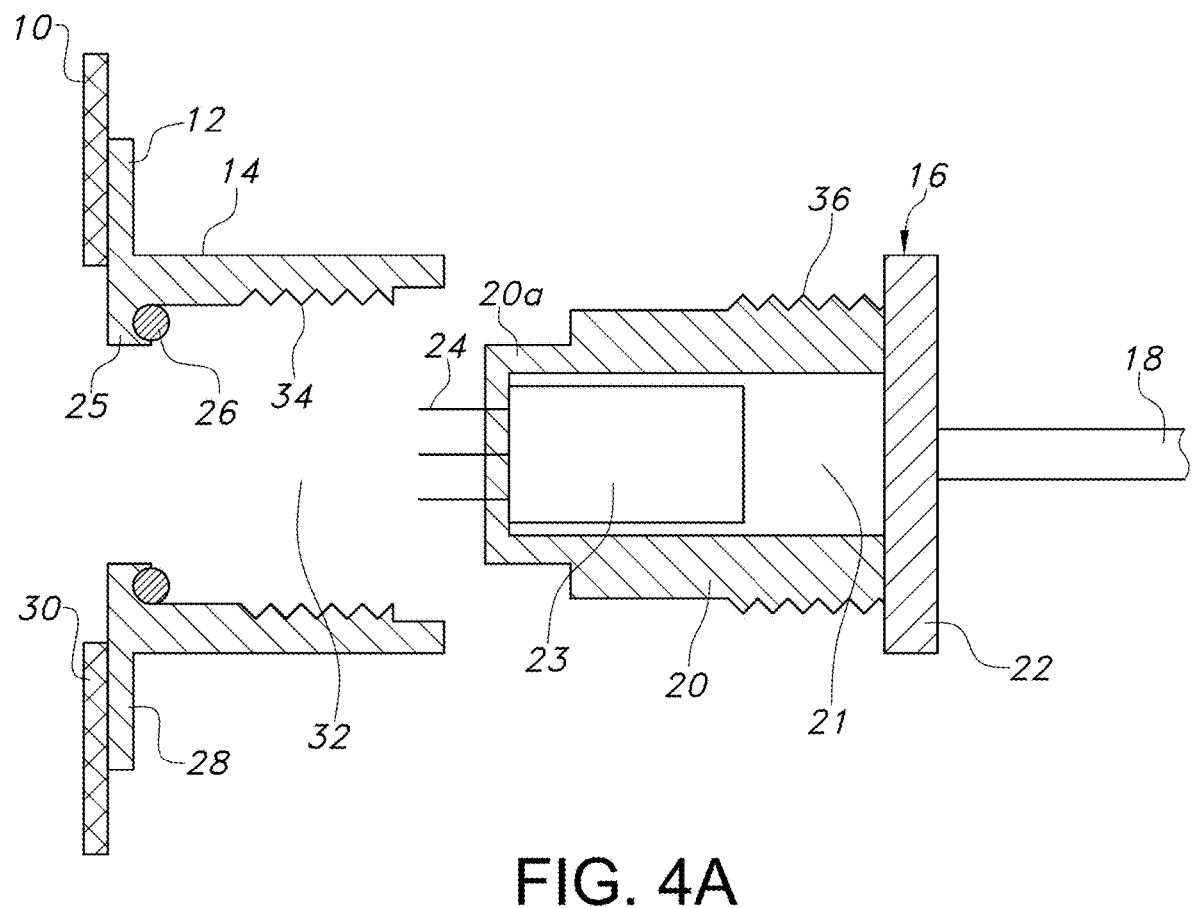
FIG. 4a is a cross-sectional view of the first embodiment shown in FIG. 4 with the O-ring seal provided at a different location.

FIG. 4 shows an O-ring 26 seated in a groove formed in a radial surface of the body portion, while FIG. 4a shows the O-ring seated in a groove formed in a sealing surface of the receptacle. The O-ring 26 of FIG. 4 will seal against an inner radial surface of the receptacle, while the O-ring 26 of FIG. 4a will seal against an axial surface of the sensor fitting.

Figure 5:
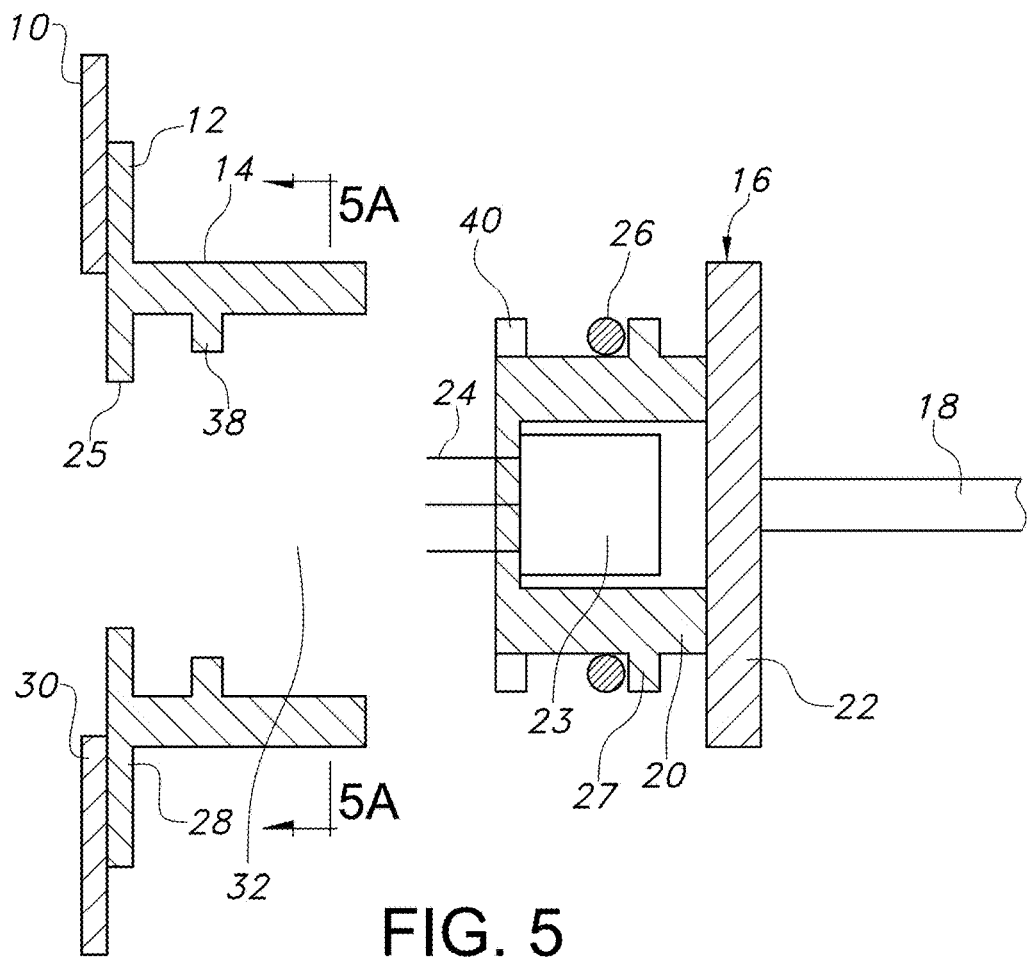
FIG. 5 is a cross-sectional view of a second embodiment of the connection between the sensor fitting and the port plate.
Figure 5A:
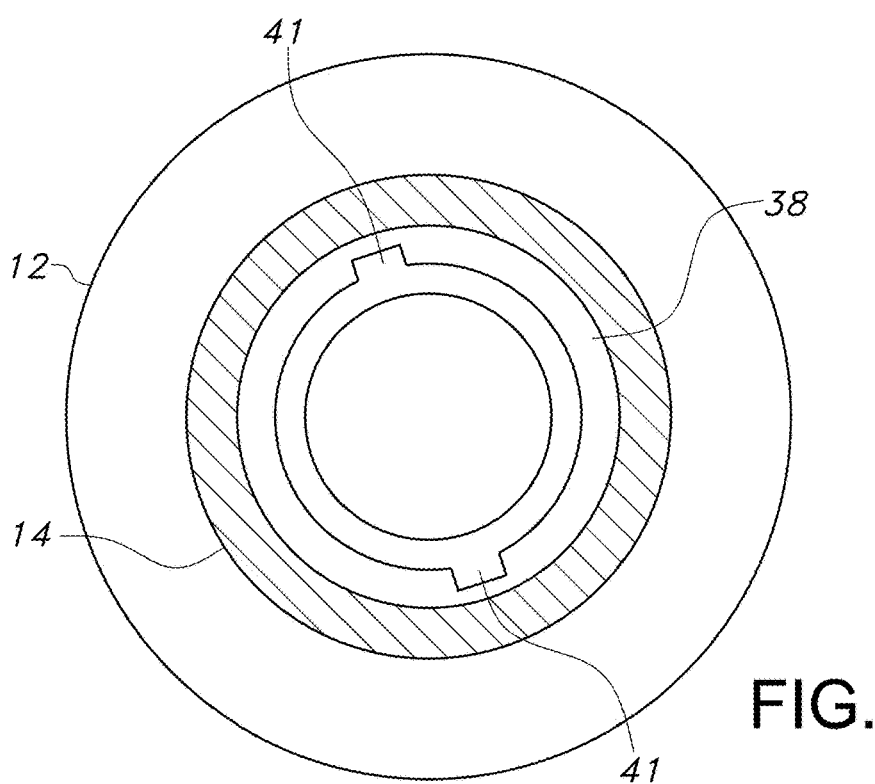

FIGS. 5 and 5a show an alternative embodiment, wherein the inner surface of the receptacle 14 is provided with one or more discontinuous ribs 38 extending radially into the passage way 32, and wherein the outer surface of the sensor body portion 20 is provided with one or more intermittent tabs 40 extending radially outward from the body portion. As can be appreciated from FIG. 5a, the sensor fitting 16 is inserted into the receptacle so that the intermittent tabs 40 pass through gaps 41 of the discontinuous ribs 38 formed in the receptacle. Upon slight rotation of the sensor fitting 16 into the receptacle 14, the ribs 38 engage the tabs 40 in a twist-lock manner to secure the sensor within the receptacle. The O-ring 26 will then be captured between the ribs 38 of the receptacle 14 and a flange 27 provided on the outside surface of the body portion 20 of the fitting.

The structure for providing the twist-lock engagement of FIGS. 5 and 5a can be designed to allow removal of the sensor fitting 16 from the receptacle 14, or additional structure can be provided to ensure permanent engagement between the receptacle and the fitting. For example, a locking tab can be provided that allows only a one-way engagement of the fitting and the receptacle so that removal of the sensor fitting from the receptacle cannot be achieved without damaging one or both elements.

Figure 6:
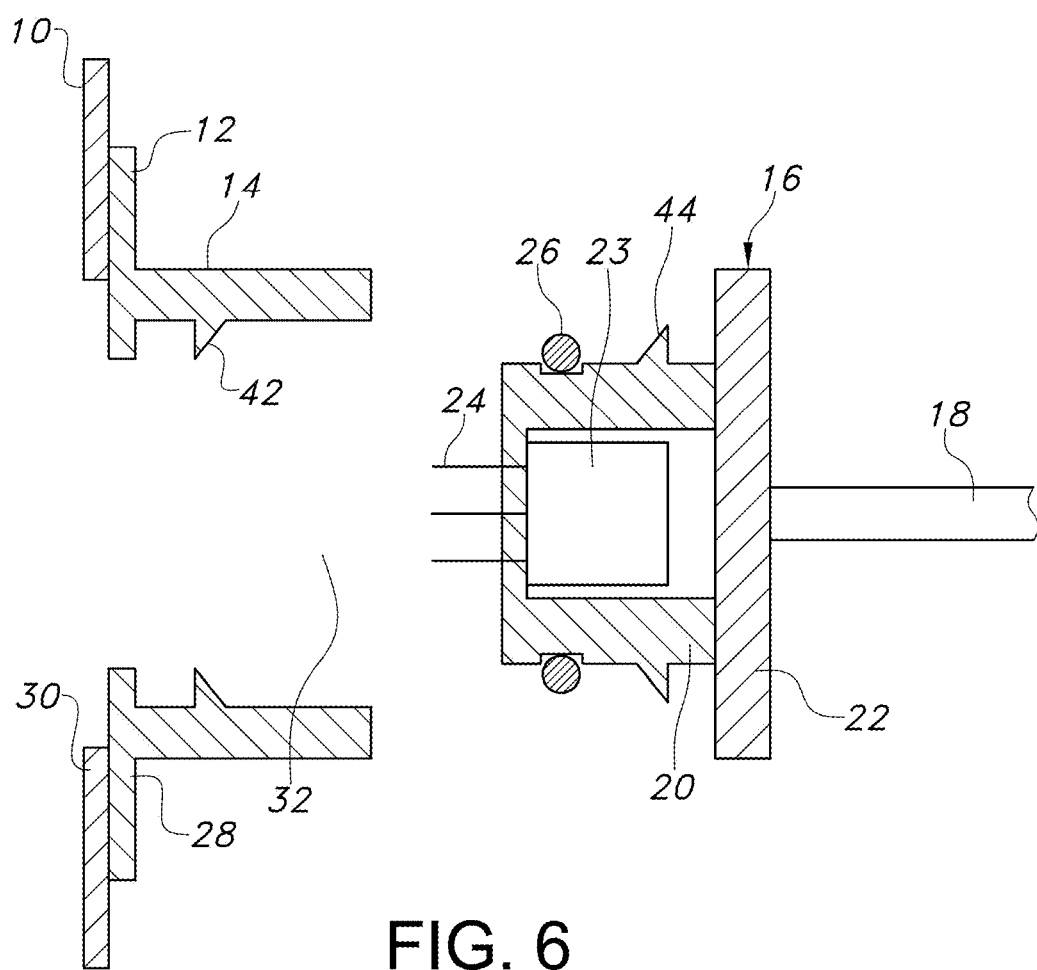
FIG. 6 is a cross-sectional view of a third embodiment of the connection between the sensor fitting and the port plate.

FIG. 6 shows yet another alternative embodiment, wherein the inner surface of the receptacle 14 and the outer surface of the sensor fitting body portion 20 are provided with cooperating detent structure 42, 44 for providing an interference snap fit between the sensor fitting 16 and the receptacle 14 upon insertion of the sensor fitting 16 into the receptacle 14. The detent structure 42, 44 can take the form of ridges having oppositely sloped flanks to permit one-way insertion of the sensor fitting 16 into the receptacle, but which will lock the fitting within the receptacle upon full insertion.

Figure 7:
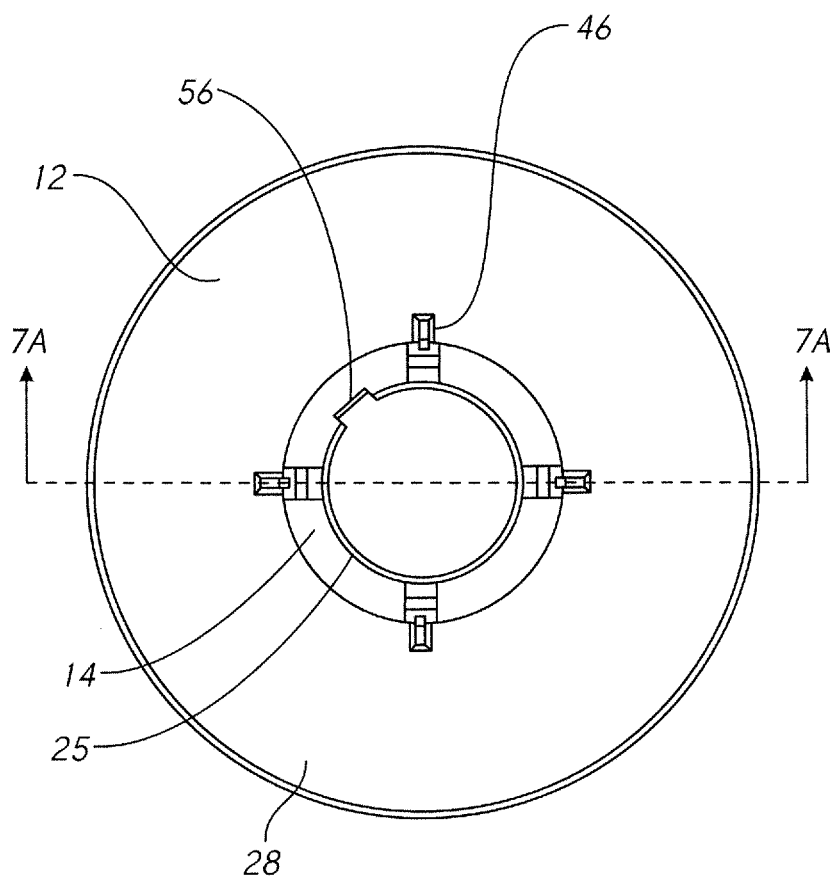
FIG. 7 is a plan view of another alternative embodiment of the port plate.
Figure 7A:
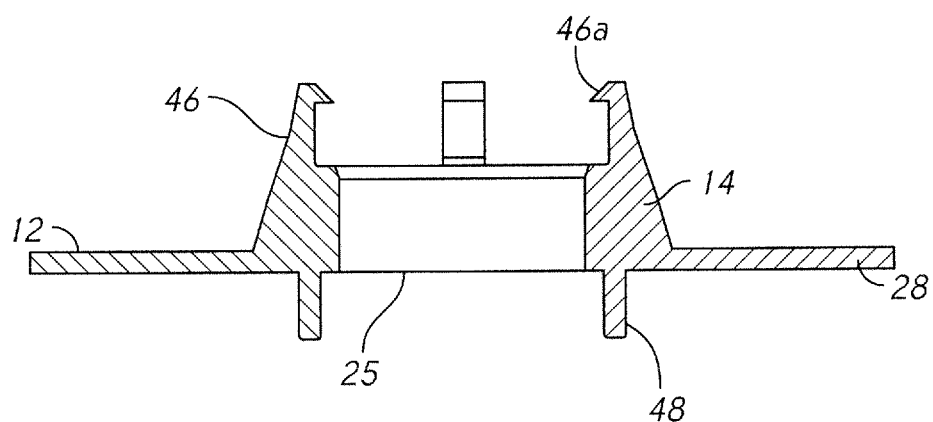

FIGS. 7 and 7a show yet another alternative embodiment of the port plate 12. The port plate 12 shown in FIGS. 7 and 7a is similar in most respects to the port plates described above. In particular, the port plate 12 has a receptacle 14 and a thin skirt portion 28 extending radially outward from the receptacle. The receptacle 14 defines an interior to accept a sensor fitting 16 and further includes a hole 25 through which the bottom of the sensor fitting will be exposed flush with the wall of the bag and the electrodes of the sensor will protrude as far as permissible into the bag.

However, in this embodiment, the port plate 12 further includes a plurality of retention tabs 46 and a plurality of guards 48 formed integrally with the port plate 12. More specifically, the plurality of retention tabs 46 protrude upwardly from the receptacle 14 in a direction away from the skirt portion. The retention tabs 46 are spaced circumferentially around the interior of the receptacle 14 and extend axially from the upper rim of the receptacle. Formed at the distal end of each retention tab 46 is a retaining hook 46a that extends radially inward towards an axis defining the receptacle interior. As will be discussed further below, the retaining hooks 46a of the retention tabs engage a retaining groove 53 formed on the sensor fitting 16 for holding the sensor fitting in place once the sensor fitting is inserted into the receptacle 14.

The plurality of guards 48 protrude outwardly from the surface of the port plate 12 opposite the surface where the receptacle 14 is formed, such that the hole 25 of the port plate 12 is positioned in between each of the plurality of guards 48. The plurality of guards 48 have a height measured from the bottom of the port plate 12 that is equal to or slightly greater than the length of the probes 24 extending from the bottom of the sensor fitting 16. With such design, the guards 48 protect both the probes 24 and the flexible storage bag 10 upon insertion of the sensor fitting 16 into the receptacle 14.

The port plate 12 of this embodiment still further includes at least one alignment slot 56 formed in an inner surface defining the interior of the receptacle 14. The slot 56 begins at the upper rim of the receptacle 14 and extends axially towards the skirt portion 28. The slot 56 has a depth to comfortably receive an alignment key 52 formed on the sensor fitting 16. As will be discussed further below, the location and the width of the slot 56 is selected to positively locate the alignment key 52 of the sensor fitting so that the probes 24 of the sensor are positioned in a desired orientation.

Figure 8:
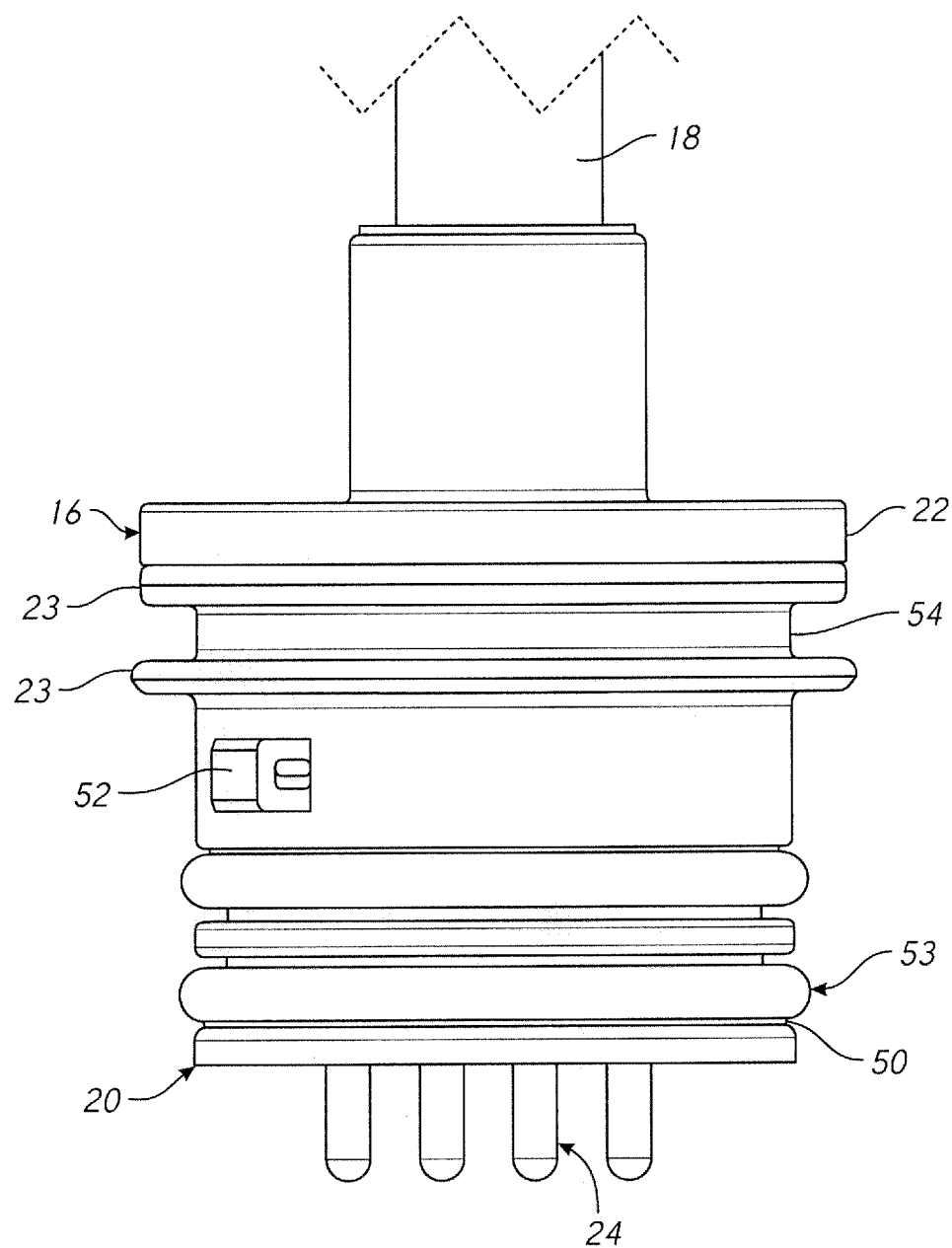
FIG. 8 is a side view of another alternative embodiment of the sensor fitting.

Referring now to FIG. 8, the sensor fitting 16 according to this embodiment is similar in most respects to the sensor fittings described above. Specifically, the sensor fitting 16 contain a sensor, which is hard wired for suitable connection to external measuring equipment via a cable 18. The sensor fitting 16 generally includes a body portion 20 and a head portion 22 provided at one end of the body portion, which together form a housing defining an inner compartment for containing the desired sensor therein.

As described above, the body portion 20 is cup-shaped with a side wall and a bottom defining a compartment therein for receiving the sensor. The head portion 22 may be molded separately from the body portion 20 and may be fixed to the open end of the side wall, opposite the bottom, to seal the compartment. The bottom is provided with suitably sized apertures, through which one or more probes 24 of the sensor can extend and protrude outwardly from the body portion from the compartment.

However, in this embodiment, the head portion 22 is formed with an annular retaining groove 54 for engaging the retaining hooks 46a of the retention tabs 46 formed on the port plate 12. The retaining groove 54 extends around the full circumference of the body portion and is bounded on its axial sides by radial walls 23 spaced apart in the axial direction.

Also in this embodiment, the body portion 20 is formed with at least one alignment key 52 extending radially from an outer circumferential surface of the body portion. As discussed above, the key 52 has a height and width to be received within the slot 56 formed in the port plate 12.

The body portion 20 of the sensor fitting 16 is further formed with one or more annular grooves 50 adjacent the bottom for receiving one or more respective O-rings 52 in a sealing manner.

Figure 9:
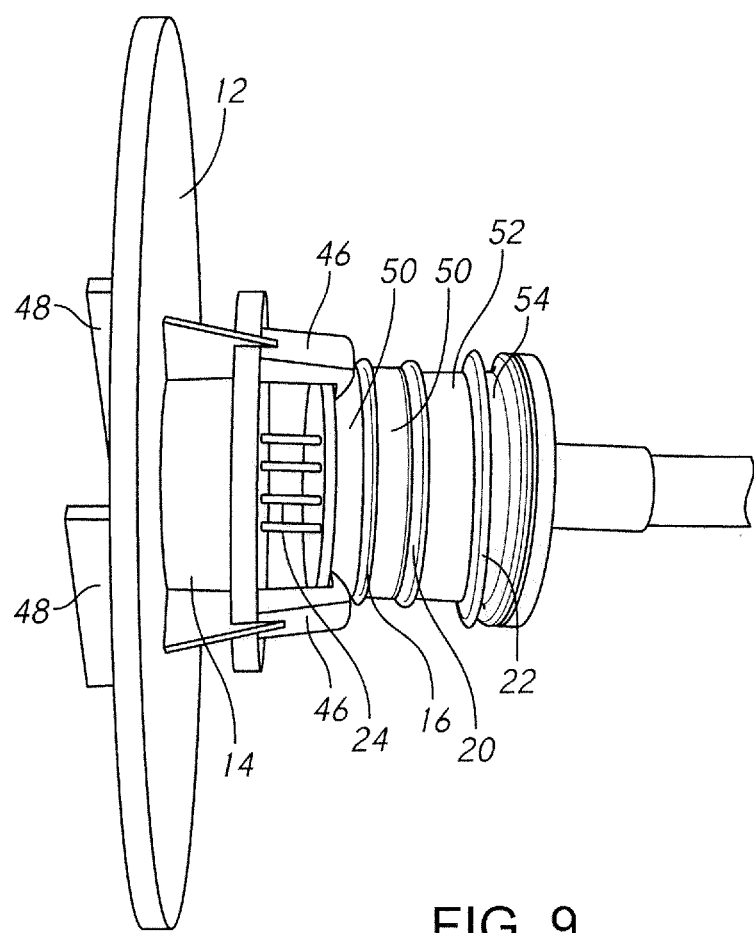
FIG. 9 is a perspective view of the connection between the sensor fitting and the port plate shown in FIGS. 7 and 8

Referring now to FIG. 9, upon assembly, the sensor fitting 16 is inserted into the interior of the receptacle 14 of the port plate 12 until the bottom of the sensor fitting becomes flush with the bottom of the skirt portion 28. During insertion, the first radial wall 23 defining the annular groove 54 of the sensor fitting 16 urges the retention tabs 46 of the port plate 12 in a radially outward direction. Further insertion allows the hook portions 46a of the tabs 46 to pass the first radial wall, wherein the resiliency of the tabs will urge the hooks in the radially inward direction to be received within the retaining groove 54. The plurality of O-rings 53 seated in each corresponding O-ring groove 50 are prevented from axial movement and make sealing contact with the interior of the receptacle 14. Also, the alignment key 52, which extends radially outwardly from the body portion 20 of the sensor fitting 16 is received within the slot 56 of the port plate 12 to prevent rotation of the sensor fitting 16.

Figure 10:
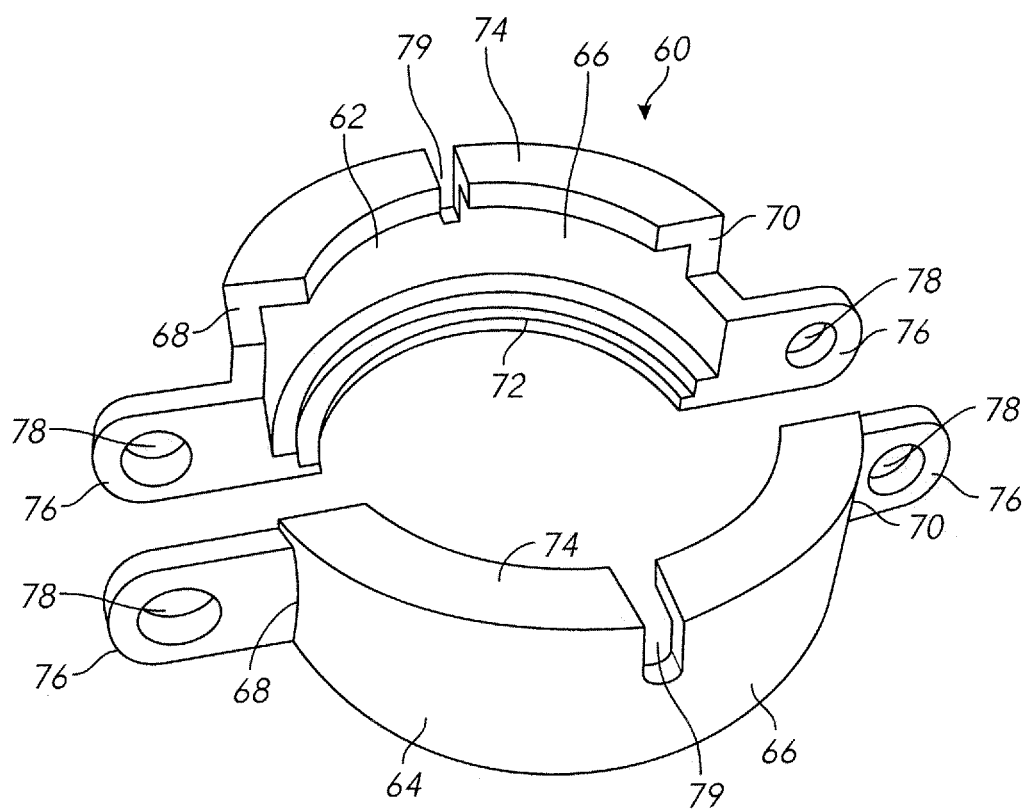
FIG. 10 is an isolated view of a collar for use in the connection shown in FIG. 9.
Figure 11:
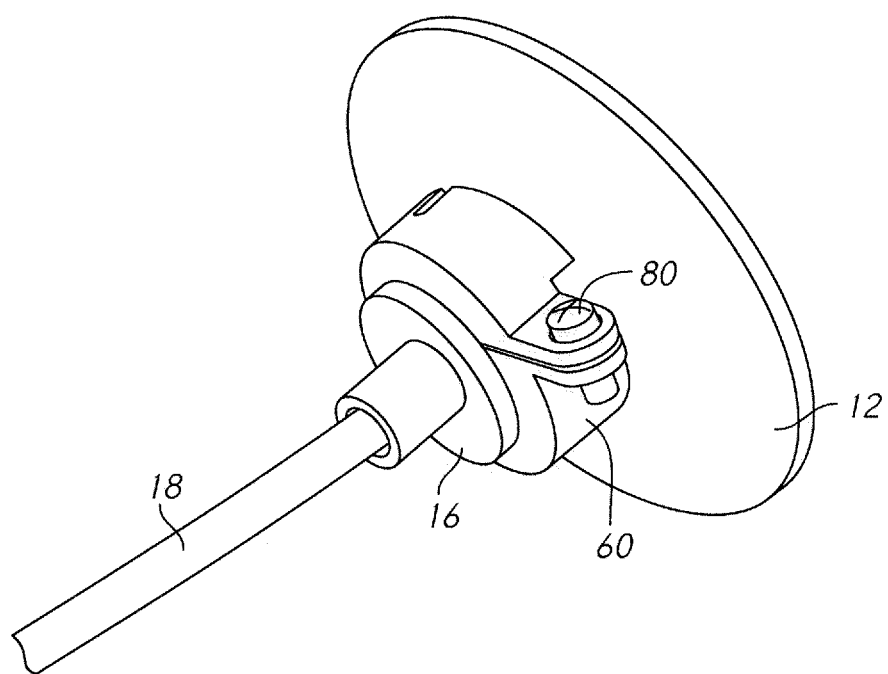
FIG. 11 is a perspective view of a connection between a sensor fitting and a port plate using the collar shown in FIG. 10.

To further enhance secure assembly of the sensor fitting 16 to the port plate 12, a collar assembly 60 can be provided, as shown in FIG. 10. The collar assembly 60 is configured and designed to surround the periphery of the receptacle 14 and sensor fitting 16 once the sensor fitting 16 is inserted into the receptacle 14 of the port plate 12. The collar assembly 60 includes two semi-circular members 62, 64, which are essentially mirror image of each other and identical. Thus, when the semi-circular members 62, 64 are placed around the receptacle 14 and sensor fitting 16 and attached together, they form a cylindrical structure that can accommodate the receptacle 14 and sensor fitting 16 therewithin, as shown in FIG. 11.

Each of the semi-circular members 62, 64 includes a wall 66 extending between opposite ends 68, 70, stair-shaped upper and planar lower extensions 72, 74 integrally connected and separated by the wall 66, and attachment members 76, each having a hole 78 therein, integrally formed at the opposite ends 68, 70 of the wall 66. The stair-shaped upper and planar lower extensions 72, 74 allow the semi-circular members 62, 64 to tightly surround the periphery of receptacle 14 and the sensor fitting 16. More specifically, once the semi-circular members 62, 64 are placed around the receptacle 14 and sensor fitting 16, the upper and lower extensions 72, 74 tightly engage with a top portion of each retaining hook 46a of the plurality of retention tabs 46 and an lower rim of the receptacle 14, respectively, with the attachment members 76 of one of the semi-circular members 62 abutting respective attachment members 76 of the other semi-circular member 64 such that the holes 78 of the attachment members align. A slot 79 is defined in the middle of the wall 66 of the semi-circular member 62, 64 such that a bottom portion of the retention tab 46 can be fitted therewithin. A fastener or connector 80 can be inserted through each aligned hole 78 to attach the semi-circular members 62, 64 together and secure assembly of the sensor fitting 16 to the port plate 12.

The port plate 12 and the sensor fitting 16 are preferably made of lightweight plastic, such as polyethylene, however other materials can be used that suit a particular application. For example, the port plate 12 and sensor fitting 16 can be made of parts that are compatible with both gamma radiation (using doses high enough for sterilization of process assemblies used in the industry, i.e., up to 45 KGy) or chemical sterilization (such as ethylene oxide (ETO)).

As mentioned above, unlike the sensor connector disclosed in U.S. Pat. No. 8,302,496, the sensor fitting 16 of the present invention does not have inlet and outlet ports with hose barbs for in-line coupling within process tubing. Furthermore the receptacle fitting design of the present invention can be used for many types of sensors to gain access for analytical measurements. The sensors and related portions of the system described herein throughout can likewise be increased in size and/or capacity to provide appropriate measurement for systems of various sizes and performance capabilities.

While various embodiments of the present invention are specifically illustrated and/or described herein, it will be appreciated that modifications and variations of the present invention may be effected by those skilled in the art without departing from the spirit and intended scope of the invention.

What is claimed is:

1. A sensor connection for a fluid process application bag comprising:
   a fluid process application bag having an opening;
   a port plate sealed around the opening of the fluid process application bag, the port plate having a hole, a receptacle defining a passage in fluid communication with the fluid process application bag, a skirt portion extending radially outward from the receptacle, and a plurality of retention tabs spaced circumferentially around the receptacle and extending axially from an upper rim of the receptacle;
   a sensor fitting having a part of a body portion seated within the passage of the receptacle and being coupled to the receptacle via the plurality of retention tabs engaging with a retention tab groove formed on a head portion of the sensor fitting; and
   a sensor contained within the sensor fitting, the sensor having at least one probe communicating with the interior of the fluid process application bag,
   wherein a plurality of guards are defined on a surface of the port plate opposite a surface where the receptacle is defined and protrude outwardly therefrom, such that the hole of the port plate is positioned in between each of the plurality of guards, and
   wherein the plurality of guards have a height measured from a bottom of the port plate that is equal to or slightly greater than a length of the at least one probe.

2. A sensor connection as defined in claim 1, wherein each of the plurality of retention tabs includes a retaining hook formed at a distal end of the retention tab for engaging with the retention tab groove to hold the sensor fitting in place once the sensor fitting is inserted into the receptacle.

3. A sensor connection as defined in claim 1, wherein the plurality of guards protect the fluid process application bag from the at least one probe upon insertion of the sensor fitting into the receptacle.

4. A sensor connection as defined in claim 1, wherein the retention tab groove extends around a full circumference of the body portion of the sensor fitting and is bounded on its axial sides by radial walls spaced apart in the axial direction.

5. A sensor connection as defined in claim 1, further comprising a plurality of O-rings in sealing engagement between an inner surface of the receptacle and an outer surface of the sensor fitting, the plurality of O-rings being seated in each corresponding O-ring groove defined in the body portion of the sensor fitting for providing a seal between the body portion of the sensor fitting and the receptacle of the port plate.

6. A sensor connection as defined in claim 1, wherein the body portion of the sensor fitting is cup-shaped having a side wall and a bottom defining an internal compartment for receiving the sensor, the probe of the sensor extending through the bottom.

7. A sensor connection as defined in claim 1, wherein the port plate further includes at least one alignment slot formed in an inner surface defining an interior of the receptacle.

8. A sensor connection as defined in claim 7, wherein the at least one alignment slot begins at the upper rim of the receptacle and extends axially towards the skirt portion and has a depth to receive an alignment key formed on the sensor fitting to prevent rotation of the sensor fitting.

9. A sensor connection as defined in claim 8, wherein the alignment key extends radially from an outer circumferential surface of the body portion of the sensor fitting.

10. A sensor connection as defined in claim 1, wherein the sensor is a conductivity sensor.

11. A sensor connection as defined in claim 10, wherein the conductivity sensor comprises at least two probes communicating with the interior of the fluid process application bag, within one of the probes an element for measuring temperature is provided and at least two of the probes being used to measure conductivity.

12. A sensor connection for a fluid process application bag comprising:
- a fluid process application bag having an opening;
- a port plate sealed around the opening of the fluid process application bag, the port plate having a hole, a receptacle defining a passage in fluid communication the fluid process application bag, a skirt portion extending radially outward from the receptacle, and a plurality of retention tabs spaced circumferentially around the receptacle and extending axially from an upper rim of the receptacle;
- a sensor fitting having a part of a body portion seated within the passage of the receptacle and being coupled to the receptacle via the plurality of retention tabs engaging with a retention tab groove formed on a head portion of the sensor fitting;
- a sensor contained within the sensor fitting, the sensor having at least one probe communicating with the interior of the fluid process application bag; and
- a collar assembly having semi-circular members to secure assembly of the sensor fitting to the port plate,
- wherein each of the semi-circular members includes a wall having opposite ends, stair-shaped upper and planar lower extensions integrally connected and separated by the wall, and attachment members, each having a hole therein, integrally formed at the opposite ends of the wall,
- wherein once the semi-circular members are placed around the receptacle and sensor fitting, the upper and lower extensions tightly engage with a top portion of each retaining hook of the plurality of retention tabs and an lower rim of the receptacle, respectively, with the attachment members of one of the semi-circular members abutting respective attachment members of the other semi-circular member such that the holes of the attachment members align, and
- wherein a fastener or connector can be inserted through each aligned hole to attach the semi-circular members together and secure assembly of the sensor fitting to the port plate.

* * * * *

UNITED STATES PATENT AND TRADEMARK OFFICE
CERTIFICATE OF CORRECTION

| | |
|---|---|
| PATENT NO. | : 10,557,811 B2 |
| APPLICATION NO. | : 15/909556 |
| DATED | : February 11, 2020 |
| INVENTOR(S) | : James F. Furey, Dennis C. Annarelli and John Benson |

It is certified that error appears in the above-identified patent and that said Letters Patent is hereby corrected as shown below:

On the Title Page

(72) Inventors:
Now reads: "Dennis C. Annarelli, Newton, PA (US)"
Should read: --Dennis C. Annarelli, Newtown, PA (US)--

Signed and Sealed this
Fifth Day of May, 2020

Andrei Iancu
*Director of the United States Patent and Trademark Office*